United States Patent [19]

Ross

[11] 3,967,616

[45] July 6, 1976

[54] MULTICHANNEL SYSTEM FOR AND A MULTIFACTORIAL METHOD OF CONTROLLING THE NERVOUS SYSTEM OF A LIVING ORGANISM

[76] Inventor: Sidney A. Ross, 6901 Katherine Ave., Van Nuys, Calif. 91405

[22] Filed: Sept. 5, 1974

[21] Appl. No.: 503,468

Related U.S. Application Data

[63] Continuation-in-part of Ser. No. 299,842, Oct. 24, 1972, Pat. No. 3,837,331.

[52] U.S. Cl. .............................. 128/1 C; 128/2.1 B
[51] Int. Cl.² ...................... A61B 5/05; A61B 19/00
[58] Field of Search .............. 128/2.1 B, 1 C, 2.1 R, 128/422

[56] References Cited
UNITED STATES PATENTS

| | | |
|---|---|---|
| 2,501,808 | 3/1950 | Brockway et al. .................. 128/1 C |
| 3,413,546 | 11/1968 | Riehl et al. ....................... 128/2.1 B |
| 3,495,596 | 2/1970 | Condict ............................. 128/422 |
| 3,753,433 | 8/1973 | Bakerich et al. ................. 128/2.1 B |
| 3,826,243 | 7/1974 | Anderson ......................... 128/2.1 B |
| 3,837,331 | 9/1974 | Ross ................................. 128/1 C |
| 3,841,309 | 10/1974 | Salter .............................. 128/2.1 B |
| 3,863,625 | 2/1975 | Viglione et al. .................. 128/2.1 B |

OTHER PUBLICATIONS

Med. & Biol. Engng., vol. 8, No. 2, pp. 209–211, 1970.
The Washington Post, Apr. 30, 1972, Sec. D3.

*Primary Examiner*—Kyle L. Howell
*Attorney, Agent, or Firm*—Blakely, Sokoloff, Taylor & Zafman

[57] ABSTRACT

A novel method for controlling the nervous system of a living organism for therapeutic and research purposes, among other applications, and an electronic system utilized in, and enabling the practice of, the invented method. Bioelectrical signals generated in specifictopological areas of the organism's nervous system, typically areas of the brain, are processed by the invented system so as to produce a sensory stimulus if the system detects the presence or absence, as the case may be, of certain characteristics in the waveform patterns of the bioelectrical signals being monitored. The coincidence of the same or different characteristics in two or more waveform patterns, or the non-coincidence thereof, may be correlated with a certain desired condition of the organism's nervous system; likewise, with respect to the coincidence or non-coincidence of different characteristics of a single waveform pattern. In any event, the sensory stimulus provided by the invented system, typically an audio or visual stimulus, or combination thereof, is fed back to the organism which associates its presence with the goal of achieving the desired condition of its nervous system. Responding to the stimulus, the organism can be trained to control the waveform patterns of the monitored bioelectrical signals and thereby, control its own nervous system. The results of the coincidence function permit results heretofore unobtainable.

41 Claims, 2 Drawing Figures

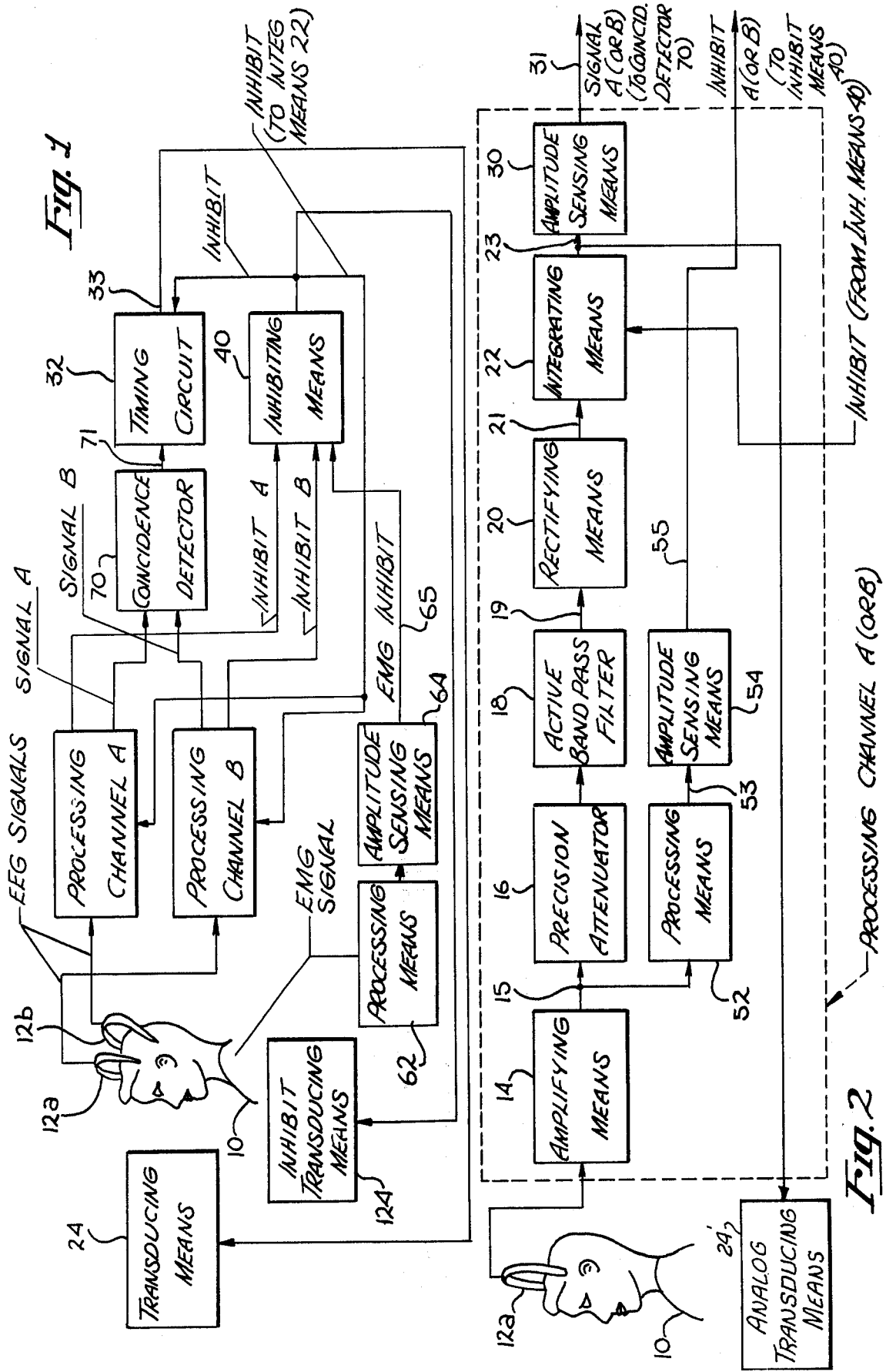

MULTICHANNEL SYSTEM FOR AND A MULTIFACTORIAL METHOD OF CONTROLLING THE NERVOUS SYSTEM OF A LIVING ORGANISM

BACKGROUND OF THE INVENTION

This is a continuation in part application of my earlier copending application filed on Oct. 24, 1972, Ser. No. 299,842, now U.S. Pat. No. 3,837,331 and I hereby specifically incorporate the disclosure of said copending application herein.

1. Field of the Invention

This invention relates in general to the field which has become known as the bio-feedback field, and more particularly to a system for processing multiple bioelectrical signals generated in the nervous system of a living organism and a method for training the organism to control the waveform patterns of its bioelectrical signals for therapeutic or other purposes.

2. Prior Art

Disorders of the nervous system, such as epilepsy, have traditionally been treated by pharmaceuticals and/or surgical procedures. The present invention is based upon the discovery that a living organism, typically an animal high on the intelligence scale, can control its brainwave and nervewave patterns and bring about permanent or long lasting changes thereto by a process of learning; and, further, that the changes induced in the bioelectrical patterns can be such as to result in the substantial control of epileptic seizures, hyper-kinesis and insomnia. This therapeutic approach has also been shown to be useful in correcting motor disorders such as the loss of motor control attributable to a spinal cord lesion. Thus, the present invention provides a safe and practical method and system enabling the application of this discovery in many fields including neurological therapy and brain research.

In the prior art, bio-feedback training has been conducted with respect to only one area of an organism's nervous system at a time. My earlier invention, disclosed in U.S. Pat. No. 3,837,331, is of this type. It discloses a means and method whereby a single bioelectrical signal is detected at a specific topological location in the nervous system of a living organism. Means are disclosed for detecting a particular electrical characteristic of interest in the single signal and, if it is present, feeding back to the organism a sensory indication of its presence. By this means and method, the organism can be trained to alter the waveform pattern of a bioelectrical signal detected in its nervous system. Heretofore, the prior art has not disclosed means or a method for training a living organism to alter multiple characteristics in the waveform pattern of a single bioelectrical signal, or multiple characteristics in the waveform patterns of a plurality of such signals. The present invention is based upon the discovery that a living organism can learn to alter multiple characteristics of one or more bioelectrical signals in its nervous system at the same time, thereby achieving new and beneficial results. In view of this discovery, the present invention teaches a means and a method by which such multiple-characteristic alteration training can be carried out.

In the case of an epileptic with a specific "focus", bio-feedback training of one area of the brain, as disclosed in the prior art, may be sufficient. However, when no focus can be located; bio-feedback training with respect to complementary area of both the right and left hemispheres of the brain may prove to be advantageous. In another, more typical case, an epileptic or insomniac may be trained to produce a specific brain wave characteristic while simultaneously depressing a different characteristic in the same or another bioelectrical signal. Thus, the present invention enables the bio-feedback training of more than one area of the organism's nervous system to take place simultaneously, or to be otherwise synchronized. Such multilateral and synchronized training has generally been found to be more effective than the sequential training of different areas of the nervous system, because it necessarily involves the concurrent and interrelated participation of all the areas. It should be noted that, in sequential bio-feedback training, the training of one area of the nervous system, e.g., the right side of the brain, has little or no effect on the other areas, e.g., the left side of the brain. A further advantage of this invention, in that training time can be substantially reduced by virtue of the capability for simultaneous training of two or more areas of the nervous system.

It should be understood that multi-signal processing, as described herein, is not just the unrelated processing of two or more signals at the same time from the same person. To the contrary, it involves the simultaneous and/or time related interaction of two or more related or unrelated characteristics of one or more bioelectrical signals of the nervous sytem.

Some biological feedback systems of the prior art often use a carrier signal modulated by the bioelectrical signal. No such modulation is part of the present invention. Systems of the prior art often include means for shifting the phase of the feedback signal with respect to the original bioelectrical signal. In the present invention, the phase relationship between the bioelectrical signal and the feedback signal is of no particular importance. Further, the present invention does not require means for impressing an electrical signal and, therefore, electrical current, into a living organism. Consequently, it is substantially safe to its subjects while they are being treated or otherwise participating in the invented method.

BRIEF SUMMARY OF THE INVENTION

The present invention is essentially a uniquely interrelated, multi-channel extension of the invention disclosed in my copending application, Ser. No. 299,842, now U.S. Pat. No. 3,837,331.

Each channel is comprised of a means for detecting bioelectrical signals generated in a specific topological region of the nervous system of a living organism, typically a human being or other intelligent animal, and means for detecting the presence or absence of particular characteristics of the detected signal. Typical means for detecting the bioelectrical signal are the electroencephalograph (EEG) recorder and the polygraph recorder. The means for detecting the presence or absence of particular waveform characteristics include conventional frequency filters, rectifiers, integrators and amplitude comparators, as more fully described hereinbelow.

As already indicated, the present invention contemplates two or more channels for processing one or more bioelectrical signals. Each channel of the invented system outputs an electrical signal which indicates the presence of one or more characteristics in the waveform pattern of the bioelectrical signal processed; e.g., the presence of certain frequencies therein, and/or a minimum signal amplitude in a particular range of frequencies. The outputs of the signal processing channels are all fed to a configuration of logical elements referred to, for convenience, as the "coincidence detector". The elements of the coincidence detector are configured to provide a discrete output only if and when a particular combination of signals are present and/or absent at the outputs of the channels, thus indicating the presence and/or absence of certain characteristics in the waveforms of the corresponding bioelectrical signal; the latter are correlated with a certain desired condition of the subject's nervous system. The coincidence detector is comprised of conventional logical elements such as AND, NAND, OR, and EXCLUSIVE OR gates.

The output, if any, of the coincidence detector is fed to a means for transducing an electrical signal into a sensory stimulus for presentation to the organism. Suitable timing circuitry may be incorporated between the output of the coincidence detector and the transducing means in applications wherein the discrete output from the coincidence detector must persist for a minimum duration before a sensory stimulus is presented. Other timing circuitry may also be incorporated to control (i) the time interval elapsing between the presentation of successive sensory stimuli (ii) the duration for which the sensory stimulus is presented, and/or (iii) the time interval during which the coincidence detector is inhibited from receiving inputs after an incorrect characteristic is detected.

The invented method requires the subject organism, utilizing its cognitive powers, to alter the particular characteristics of the detected bioelectrical signals so as to cause the sensory stimulus presented to it to change in a preconceived manner; e.g., turn on a light or advance a counter. The preconceived condition of the sensory stimulus is, of course, related to certain desired waveform patterns of the originally detected bioelectrical signals, or more specifically, to the attainment of one or more desired characteristics in those signals.

By repeatedly exercising a subject in the manner just described, i.e., by extensive training utilizing the present invention, the subject can learn to control its brainwave or nervewave patterns for therapeutic or other purposes. For example, the present invention can be used to help eliminate certain frequency components found in the brainwave patterns of persons suffering from epilepsy. In cases of epileptic cerebral behavior, where no specific focus is located, bioelectrical signals may be taken from each hemisphere of the brain and processed simultaneously through separate channels of the invented system. Thus, pertinent characteristics of the two hemispheric brainwave patterns may be correlated and cerebral behavior peculiarly related to bilateral activity may be detected and modified.

The topological locations, in the organism's nervous system where detection is to take place is a function of the user's objective. Thus, if the present invention is to be used for epileptic therapy, the regions of the brain known to be involved in epileptic seizures would be subjected to the EEG investigation. Conversely, where there is now inadequate correlation between the topology of the nervous system and its functions, the present invention provides a useful research tool capable of substantially enhancing the topological "mapping" of an organism's nervous system.

The particular characteristics of the detected bioelectrical signal which are of interest to the user are also a function of his objective. In the case of epileptic therapy, for example, the presence and amplitude of certain frequency components in the clinical EEG have been correlated with seizures. Thus, in the latter application, it is the frequency spectrum of the bioelectrical signal which is of interest. In other applications it may be desirable or necessary to detect the coincidence or non-coincidence of particular waveform characteristics in two or more bioelectrical signals, or the presence or absence of electrical or electrochemical activity at one or more locations in the nervous system. In still other applications, the duration for which certain bioelectrical signals are present may be a significant parameter requiring detection. For this reason it should be understood that the invented system is not a fixed single structure but rather a basic combination of means whose specific embodiments are adapted to suit particular applications. Similarly, the invented system is typically tuned and calibrated in accordance with the requirements of each application to which it is to be applied. This invention also contemplates the combination of means sufficient to enable multi-purpose use in a number of applications either simultaneously or by sequential selection.

Thus, it is a principal object of this invention to provide a practical and safe method and system to enable a living organism to control significant characteristics of its nervous system.

Another principal object of this invention is to provide a therapeutic means for the control of certain disorders of the nervous system.

A still further object of the invention is to provide a flexible tool for neurological research including topological mapping of the nervous system.

Other objects, novel features and advantages of the present invention will become apparent upon making reference to the following detailed description and the accompanying drawings. The description and the drawings will also further disclose the characteristics of this invention, both as to its structure and its mode of operation. Although a preferred embodiment of the invention is described hereinbelow, and shown in the accompanying drawings, it is expressly understood that the description and drawings thereof are for the purpose of illustration only and do not limit the scope of this invention.

BRIEF DESCRIPTION OF THE DRAWINGS

FIG. 1 is a block diagram of a two channel embodiment of the invented system.

FIG. 2 is a functional block diagram of the elements comprising each of the channels of the invention of FIG. 1.

DETAILED DESCRIPTION OF THE INVENTION

With reference to FIGS. 1 and 2, a two channel embodiment of the invented system is now described in detail. Like elements in each Figure will be designated by like numerical designations. The invented method will be described in conjunction with the description of the operation of the system. For the purposes of this description, the living organism will be a human being and the portion of the nervous system involved will be the brain. It should be understood, however, that the invention is not limited to two channels, nor are its applications limited to human beings or to bioelectrical signals originating in the brain.

In FIG. 1, a human subject 10 is shown with two conventional sets of electrodes 12a and 12b affixed to his skull. The electrodes 12a and 12b detect the bioelectrical signals generated in the topological regions of the brain at which they are affixed, such signals being commonly referred to as "EEG signals". The electrodes 12a are connected to the input of Channel A while the electrodes 12b are connected to the input of Channel B of the invented system. Typically, the structures of Channels A and B are the same. That structure is now described with reference to FIG. 2.

The EEG signal coming into Channel A or B is first fed to amplifying means 14. Amplifying means are typically incorporated in commercial EEG and polygraph recorders. When a recorder is used to provide the amplifying means, the EEG signal may, of course, be displayed on the output chart paper. Such display of the EEG signal is advisable at the onset of the training and periodically thereafter for the benefit of the therapist in charge of the operation.

The amplified EEG signal is then routed to a precision attentuator 16 in series with an active precisely calibrated and tuned bandpass filter 18, i.e., a filter having some gain. Filter 18 is required in applications wherein a particular frequency band is of interest because its presence, energy content and/or duration of its presence are parameters of significance to the therapeutic or research objective of the user. In any event, some filtering is typically required in order to filter out undesired EEG frequencies and other signals attributable to cardiac and muscular responses as well as noise from the ambient environment. The precision attenuator is adjusted so that the filtered signal appearing at the output 19 of the bandpass filter 18 has a sufficient amplitude, typically one volt, peak to peak. A terminal may be provided at output 19 of filter 18 to enable the display of the filtered EEG signal. Such a display can be of use during operation of the system. When an EEG or other recorder is used, the signal at the point 19 may be patched to one of the recording tracks of the recorder, since most commercial recorders provide means for such external inputs.

The filtered EEG signal is then passed through means for rectifying 20. In multi-signal applications, where the sensory stimulus fed back to the subject is typically a discrete stimulus, e.g., a counter display, indicating the presence of the desired combination of bioelectrical signals or particular waveform characteristic thereof, half wave rectification is usually adequate. The output 21 of the rectifying means 20 is a unipolar signal whose peak amplitude is directly proportional to the amplitude of the frequency components passed by the filter 18; thus, the rectified signal is a measure of the presence of, and energy in, the selected frequency band of the EEG signal. A terminal may be provided at point 21 of rectifying means 20 for purposes of display.

Following rectification, the rectified signal is typically integrated by an integrating means 22 such as for example, an operational amplifier integrator, having a charge time constant Tc and a discharge time constant Td. The values of Tc and Td are selected so that, for a particular frequency band, the signal at output 23 of integrating means 22 is directly proportional to the RMS amplitude of the rectified signal at point 21. When, for example, the frequency of the filtered EEG signal is about 13 Hz, Tc and Td are set at approximately ¼ second. In addition, the aforesaid value of Tc and Td substantially eliminates flickering of any light source driven by integrating means 22 to provide the sensory stimulus to the subject. Flickering, of course, is typically disturbing to the subject 10. Integrating means 22 also acts as a filter of any high frequency components of the rectified signal, as well as of any noise spikes passing through. As elsewhere in the invented system, a terminal may be beneficially placed at point 23 to enable the monitoring of the output of the integrating means 22.

In some applications the magnitude of the detected characteristic of the EEG signal is a significant parameter. Typically, these are applications where bioelectrical activity within a certain frequency band is of significance only if it is of a particular magnitude. For these applications, amplitude sensing and comparing means 30 is employed between the integrating means 22 and the output of the channel for the purpose of further processing the signal. The means for sensing amplitude 30 receives the integrated signal present at point 23. The amplitude sensing means 30 may include voltage comparator circuitry, Schmitt triggers or relay tripping circuitry, to name just some of the possibilities. The basic function of the amplitude sensing means 30 is to provide a signal at its output 31 only if and when the signal at its input 23, typically the integrated signal, has an amplitude of some minimum or specific magnitude. The output of the means for sensing amplitude 30, typically a discrete voltage, is the output of Channel A or B. Its appearance indicates the presence in the bioelectrical signal processed of the filtered frequencies having at least the minimum amplitude specified.

With reference to FIG. 1, the overall system is now described. The outputs of Channels A and B are fed to coincidence detector 70. Coincidence detector 70 is comprised of a suitable configuration of logical elements, such as, for example, AND, NAND, OR and EXCLUSIVE OR gates, the configuration being adapted to the particular application. Many such logical elements are commercially available and widely used in the electronics field. Suppose, for example, that the simultaneous presence of discrete signals out of Channels A and B (hereinafter referred to as signal A and signal B respectively) correlates with a desired condition of the subject's nervous system. In such a case, the coincidence detector 70 need only be a simple logical AND gate. If, on the other hand, the desired condition is manifested by the absence of both signal A and signal B, a NOR gate could implement coincidence detector 70. When the presence of signal A and the absence of signal B manifests the desired condition, an AND gate, having an inverter in the input line receiving signal B, would be used. In addition, this invention contemplates the non-simultaneous presence and/or absence of the particular electrical characteristics of interest as a coincidence warranting the presentation of a reward to the subject 10. To illustrate this application, assume that a desired condition of the nervous system is manifested by the appearance of signal A first and, after a short delay, the appearance of signal B. The coincidence detector 70 would then have (i) a means for storing signal A, such as, for example, a conventional flip-flop; and (ii) a pair of conventional one-shots electrically coupled in series. Signal A would trigger the first one-shot, the latter having an output duration equal to the minimum delay which should exist between the appearance of signals A and B. The second oneshot, in turn, is triggered by the falling off of the output of the first one-shot. The duration of the output of the second one-shot is approximately the interval within which signal B must appear if a reward is to be provided. Thus, it is during this second interval that the coincidence of signal A, stored in the memory means, and signal B must occur.

The present invention contemplates coincidence detector 70 having all of the foregoing logical elements selectively available, and means for switching signal A and signal B to the appropriate elements as required. Moreover, in application involving a large number of bioelectrical signals and corresponding channels, it is within the scope of the present invention that coincidence detector 70 may be a programmable, digital computer with appropriate analog to the digital and digital to analog conversion means.

Preferred embodiments of this invention include a timing circuit 32 which provides additional control functions governing the sensory stimulus which is to be fed back to the subject 10. Timing circuitry 32 is normally driven by the output 71 of the coincidence detector 70. Its output, in turn, is electrically coupled to a transducing means 24, which generates the sensory stimulus presented to the subject 10. Timing circuit 32 provides whatever timing functions are required by the particular application such as, for example, (i) sensing the duration of the output of coincidence detector 70; (ii) controlling the intertrial interval and/or (iii) controlling the duration of the sensory stimulus presented to the subject 10. It drives transducing means 24 in accordance with any one or all of the foregoing timing functions. For example, the duration sensing function, implemented by conventional timing circuits, determines whether a signal at the output 71 of coincidence detector 70 persists for a minimum or other specified duration. The persistance of the output signal at point 71 is a condition which must be satisfied before the timing circuit 32 will drive transducing means 24.

The intertrial interval control function controls the time interval elapsing between the presentation of successive sensory stimuli to the subject 10. When, for example, the subject 10 is stimulated by a discrete change in a visual counter, the intertrial interval control function determines the minimum time interval before an advance in the number display can be made. This feature enables the subject 10 to see and appreciate the reward for his efforts represented by the advance in the number display. The sense of being rewarded is typically diminished in a subject 10 when the sensory stimulus is changing too rapidly.

The control functions of the timing circuit 32 may be selectable or variable, i.e., timing circuit 32 may include means for continuously or discretely changing the various timing criteria. These functions and capabilities may be readily implemented by conventional electronic circuits known in the electronics field.

In some applications it is desirable to provide a means for inhibiting the presentation of a sensor stimulus to the subject 10 under certain conditions. Such an inhibiting means 40 is shown in FIG. 1 electrically coupled to the timing circuit 32 and integrating means 22. When a condition requiring suppression of a sensory stimulus to the subject 10 is detected, inhibiting means 40 prevents any signal from appearing at the output 33 of the timing circuit 32. Inhibiting means 40 can be implemented by electronic circuits known in the field; e.g., if timing circuit 32 requires a charging circuit to fire in order to produce an output at point 33, the inhibiting circuit can be designed to discharge the charging circuit upon detection of a condition requiring suppression of the sensory signal. Similarly, inhibiting means 40 can be used to also discharge the capacitor of integrating means 22.

Conditions typically requiring suppresion of the sensory signal include, but are necessarily limited to, (i) the presence of a particular frequency in a bioelectrical signal; (ii) excessively high EEG signal amplitudes at one or more points in the system; (iii) epileptic spikes characteristically observed during an epileptic seizure; and (iv) the presence of excessive "noise" attributable to bioelectrical activity in the subject's muscular apparatus; i.e., the subject's electromyograph (EMG). In epilepsy therapy it has been observed that an epileptic seizure produces characteristic spikes within the frequency band of a normal brainwave pattern. These epileptic spikes often have high amplitudes, or they "ride" atop the amplitude waveform of the EEG signal, thereby reaching high levels at their peaks. If such spikes appear during a therapeutic session, their presence, superimposed on a normal brainwave pattern, is inconsistent with the presentation of a sensory stimulus (which is an indication of a favorable brainwave pattern; i.e., a "reward" to the subject). With reference to excessively high EEG signal amplitudes, such amplitudes are undesirable because they can produce a false feedback stimulus to the subject 10. For example, a bioelectrical signal may have a very low amplitude frequency component within the band pass of the filter 18; i.e., very little of the desired characteristic. However, because of the roll-off characteristic of the filter 18 and the high amplitude of the signal, a sufficiently large signal could pass through the filter, causing the remainder of the system to respond as though the desirable characteristic had been detected. Thus, the detection of excessively high EEG signal amplitudes and the consequential inhibition of a sensory stimulus to the subject 10 makes the system respond as through the roll-off characteristic of filter 18 were ideal; i.e., that it has an infinite slope.

With reference to FIG. 2, the detection of a particular frequency, the presence of excessively high EEG signal amplitudes or characteristic epileptic spikes requires processing means 52 and a second amplitude sensing means 54. The EEG signal is picked off at the output 15 of amplifying means 14 and passed through processing means 52 before being input to amplitude sensing means 54. Processing means 52 is a convenient representation of a series of elements comprising a precision attenuator, an active filter, rectifying means and integrating means having a very short charging time constant Tc. When spikes or excessively high amplitudes are the conditions for inhibit, the filter in processing means 52 is very broadband. In such cases, processing means 52 passes substantially all of the frequency components of the EEG signal with minimum delay. However, when the presence of a particular frequency is the condition requiring an inhibit, the filter in processing means 52 is set to narrowly pass just that frequency. If the amplitude of the EEG signal appearing at the output 53 of processing means 52 is determined by amplitude sensing means 54 to be above a predetermined magnitude, an inhibit signal appears at its output 55. The presence of an inhibit signal at point 55 activates inhibiting means 40.

Detection of excessive muscular noise is done by means of electrodes (not shown), affixed to the body of the subject 10 at an appropriate location, in conjunction with an EMG recording. With reference to FIG. 1, the detected EMG signal is amplified, filtered, rectified and integrated by processing means 62 in a manner similar to that described hereinabove with respect to the EEG signal. It should be understood that processing means 62 is merely a convenient representation of a series of elements comprised of amplifying means, precision attenuator, active bandpass filter, rectifying means and integrating means. Amplitude sensing means 64 receives the processed EMG signal. If the amplitude of the processed EMG signal is determined by the amplitude sensing means 64 to be above a predetermined magnitude, an inhibit signal appears at its output 65. The presence of an inhibit signal at point 65 activates inhibiting means 40.

It should be understood that in multi-channel configurations of the present invention, all or none of the channels, or any subset thereof, may have the above-described means for detecting inhibit conditions such as, for example, excessively high EEG signals, epileptic spikes and/or noise generated in the subject's muscular apparatus.

It is often desirable to control the duration of the inhibit mode once an inhibit condition is detected. For example, when epileptic spikes are detected, it is desirable, for the sake of the subject, to ensure that there is no further sensory stimulation fed back for at least two seconds, even if the appearance of the spikes is only momentary. For this purpose, a re-triggerable one-shot located within inhibiting means 40 and set to provide a two second output, can provide the means for controlling the inhibit mode duration; i.e., for maintaining the discharge of the timing circuit 32 and integrating means 22 for at least two seconds. Of course, the specific duration of the output of the one-shot depends upon the particular application.

In certain embodiments of this invention, it is desirable to provide a sensory stimulus indicating the fact that the system is in an inhibit mode. For this purpose the re-triggerable one-shot, located within inhibiting means 40, can also be used to drive an inhibit transducing means 124, typically comprised of one or more visual displays and/or auditory means such as one or more buzzers. Each sensory stimulus indicating an inhibit is distinct from every other. Thus, for example, different colored visual displays may be used to indicate each of the detected conditions which may cause an inhibit. The re-triggerable one-shot ensures that the inhibit indication is displayed for at least 1–2 seconds, thereby eliminating flickering.

Transducing means 24 provides the sensory stimulus to the subject 10 in response to an output from timing circuit 32. An output from timing circuit 32 indicates that all frequency, amplitude, coincidence and duration conditions have been satisfied and that no inhibit conditions are present. Transducing means 24 typically provides a visual or audio stimulus, or combination thereof, to the subject 10 as a reward for having achieved the desired waveform patterns. A preferred transducing means 24 is a light display comprised of two rows of numbered lamps driven by an electronic counter. One row of lamps designates "tens" while the second row designates "units". Only one lamp in each row is lit at any given time. The subject 10 can readily read the number by observing which numbered lamp is lit in each row. When the desired characteristic is detected in the EEG signal, the subject 10 is rewarded by observing an increase in the number displayed by the lamp. A single chime may accompany each advance of a units lamp and a double chime each advance of a tens lamp, thereby adding audio stimulation to the subject. In another embodiment, the rows of tens lamps are omitted and a single lamp, typically green, is momentarily illuminated as the counter advances to the next count. The digital readout of the counter may also be displayed in both of the above embodiments of transducing means 24.

It should be understood that while only one embodiment of this invention has been described in detail, many variations are possible as a function of the requirements of each application. For example, in some application, rectifying and integrating means 20 and 22 respectively, may not be required; i.e., the amplitude sensing means 30 may directly receive the filtered signal at point 19. In other cases, the integrating means 22 alone may be eliminated. The appropriate configuration for a given application can be readily determined by persons skilled in the subject field. For example, when two or more waveform characteristics are being trained concurrently, it may be desirable to provide a sensory stimulus related to each one. In such applications, the coincidence detector 70 and timing circuit 32 of FIG. 1 may be by-passed and the output of each channel displayed on a multi-display transducing means 24. (A timing circuit 32 may, however, be incorporated on any channel where appropriate.) A multidisplay transducing means 24 suitable for such applications comprises two or more vertical side by side rows of lamps, one for each characteristic being trained. The subject 10 can then see how well he is able to produce the desired waveform characteristics at the two or more areas of his nervous system with respect to which he is training. He can see and compare his relative success in the different areas of interest; the more lamps illuminated in a row, the more success in that channel.

For certain applications, another variation of the present invention is to electrically couple the output 23 of integrating means 22, in any channel, directly to a separate transducing means 24' for that channel. In such applications, the sensory stimulus presented to the subject 10 is an analog of the characteristic of interest in the EEG signal. Preferred transducing means 24' which provide such an analog sensory stimulus include (i) a light emitting diode, (ii) an incandescent lamp or illuminating panel whose intensity of illumination is proportional to the voltage applied across it, (iii) an audio device whose sound intensity is directly related to the voltage applied to it, and (iv) a linear row of lamps. In the latter means, the number of lamps which are lit is proportional to the voltage applied. When the driving voltage (the output of integrating means 22) is near zero, all the lamps are off. As the voltage increases, the first or bottom-most lamp starts to illuminate. When the first lamp approaches its maximum illumination, the next lamp above begins to illuminate. This sequence continues until all the lamps are fully illuminated, corresponding to a fully charged integrating means 22. The operation is bilateral; i.e., the lamps go off from top to bottom as the driving voltage decreases.

Many combinations of sensory stimuli are possible with the multi-channel configuration of this invention.

For example, certain channels may be coupled to the coincidence detector 70 and to timing circuit 32, as shown in FIG. 1, the latter driving a first transducing means if all the waveform characteristics of interest are present or absent as the case may be; while, on the other hand, the outputs of integrating means 22 in other channels may be coupled directly to separate transducing means to provide stimuli porportional to the strength of the desired characteristics detected in bioelectrical signals processed by those channels.

The inventive method is practiced using the abovedescribed system. The subject 10 is first placed in a position relative to the transducing means 24 which will enable the sensory stimulus produced by such means 24 to stimulate him; e.g., enable him to see the display lights, digital counter and/or hear an audio tone. The subject 10 is then fitted with electrodes 12 at the specific topological areas of his nervous system selected by the therapist or experimenter. The precision attenuator 16 and bandpass filter 18 are properly adjusted and calibrated and timing criteria, if any, are set into the timing circuit 32; likewise, any amplitude criteria are set into the amplitude sensing means 30. Typically, the filter 18 is selected to pass desired frequencies detected in the EEG signal, i.e., frequencies which have been correlated with particular brainwave or nervewave patterns. Likewise, the amplitude and duration criteria are also related to particular patterns of interest. In the case of epileptic seizure suppression, for example, the center frequency of active bandpass filter 18 is typically set at about 13 Hz. The gain of the precision attenuator is set to produce a peak to peak voltage in the range of 0–3 volts at output 19 of bandpass filter 18. The amplitude sensing means is set to provide an output if the signal at point 19 has a peak to peak amplitude of at least one volt for a few cycles. With reference to the timing circuit 32, the duration sensing function is typically set to respond to durations of the desired characteristic of from ½ to 1 second. Typical intertrial intervals are from 1–5 seconds. The coincidence detector 70 is set to detect the desired conditions (paradigm).

Bioelectrical signals may be detected at different areas in the nervous system and each coupled to a separate channel of this invention. In addition, a single bioelectrical signal may be coupled to more than one channel for the concurrent detection of different characteristics thereof.

The presence of the sensory stimulus, in increased intensity and/or its advancement (as in the case of a counter) is an indication to the subject 10 that the desired waveform patterns are present. Thus, the subject 10 is instructed to concentrate, think and/or use his willpower so as to obtain the sensory stimulus, increase its intensity or advance it, as the case may be. In some applications, the subject 10 may be rewarded when he is able to produce a certain characteristic in the waveform of a particular bioelectrical signal, while simultaneously suppressing a different characteristic in the waveform of the same signal. In other applications, the reward is given when the subject produces a desired characteristic in the waveform of one bioelectrical signal, while simultaneously suppressing a different characteristic in the waveform of a different signal. These are just two examples of many possible applications of the present invention.

After a period of intensive training in the practice of the invented method, the subject 10 can bring about permanent or long lasting changes to the characteristics of selected brainwave or nervewave patterns. For therapeutic purposes, certain desired characteristics can be enhanced while undesirable characteristics reduced, resulting in a beneficial change in the subject's clinical EEG. Further, the present invention can be of value in analyzing the subject's clinical EEG. While it is not yet clear how and in what manner the subject's cognitive powers bring out changes in the brainwave or nervewave patterns, such results have been observed and reported. When timing circuit 32 is utilized, the required duration of a desired characteristic may be gradually increased so that the subject 10 must strive further in order to achieve the reward. This aspect of the method is analogous to the procedure of increasing the number of exercises in a program of physical training.

Other variations and applications of the invented method will be apparent to persons skilled in this field without departing from the spirit and scope of this invention. This invention, therefore, is not intended to be limited to the particular method disclosed herein.

I claim:

1. A method of controlling the nervous system of a living organism comprising the steps of:
   a. detecting one or more bioelectrical signals from one or more topological locations in said organism's nervous system;
   b. passing said one or more bioelectrical signals through a plurality of electronic means responsive to the presence of at least one electrical characteristic of interest in the waveform of a bioelectrical signal, each of said responsive means being adapted to provide a first output signal whenever said electrical characteristic of interest is present;
   c. determining by electronic logic means when said plurality of first output signals, or any subset thereof, is present or absent in a predetermined manner indicative of a desired condition of said organism's nervous system, said logic means being adapted to provide a second output signal when said desired condition is indicated;
   d. transducing said second output signal into a discrete sensory stimulus capable of stimulating at least one of the senses of said organism; and
   e. causing said organism to concentrate mentally so as to produce or change the state of said discrete sensory signal;
   whereby said organism is trained to alter the waveform pattern of said one or more bioelectrical signals, said discrete sensory stimulus being presented to said organism as a reward for producing our suppressing said electrical characteristics of interest in said one or more signals, thereby achieving said desired condition of said nervous system.

2. The method of claim 1 wherein said electrical characteristic of interest in any of said bioelectrical signals is:
   i. a preselected frequency component thereof;
   ii. an amplitude thereof greater than a preselected minimum; or
   iii. a preselected frequency component thereof having a preselected minimum amplitude.

3. The method of claim 2 wherein said preselected minimum amplitude is any detectable amplitude greater than zero.

4. The method of claim 1 wherein one bioelectrical signal is detected from one topological location in said organism's nervous system and passed through a plurality of said responsive means.

5. The method of claim 1 wherein a plurality of bioelectrical signals is detected from a plurality of topological locations in said organism's nervous system and passed through a corresponding plurality of said responsive means.

6. The method of claim 1 wherein a plurality of bioelectrical signals is detected from a plurality of topological locations in said organism's nervous system, and wherein at least one of said bioelectrical signals is passed through at least two of said plurality of responsive means, and said other bioelectrical signals, if any, are each passed through one of said responsive means.

7. The method of claim 1 including, following step (c) thereof, the additional step of passing said second output through a timing circuit adapted to detect whether said second output is present for a preselected minimum duration and to pass said second output signal only if it persists for said minimum duration.

8. The method of claim 1 wherein in step (c) thereof, said plurality of first output signals, or any subset thereof, are determined to be present or absent concurrently.

9. The method of claim 1 wherein in step (c) thereof, at least two of said plurality of first output signals are determined to be present or absent sequentially in time.

10. The method of claim 1 including, following step (d) thereof, the additional step of controlling by electronic timing means the duration of the presentation of said sensory stimulus to said organism.

11. The method of claim 1 including, following step (a) thereof, the additional steps of:
   i. passing at least one of said bioelectrical signals through second electronic means responsive to the presence of an electrical characteristic of interest in the waveform thereof and adapted to provide a third output signal which is an electrical analog of said characteristic of interest, if present; and
   ii. transducing said third output signal into a sensory stimulus which is also an analog of said characteristic of interest, said stimulus being capable of stimulating at least one of the senses of said organism, said analog sensor stimulus being presented to said organism as a reward for producing said corresponding bioelectrical signal having said characteristic of interest.

12. The method of claim 1 including, before step (d) thereof, the additional steps of:
   i. detecting the presence of at least one undesirable electrical characteristic in the waveform of at least one of said bioelectrical signals; and
   ii. inhibiting the appearance of said second output signal by electronic inhibit means when and if said undesirable electrical characteristic is detected;
   whereby, said method is inhibited by inhibiting the presentation of said discrete sensory stimulus to said organism.

13. The method of claim 12 wherein said undesirable electrical characteristics in said bioelectrical signal is:
   i. a preselected frequency component thereof;
   ii. an amplitude thereof greater than a preselected magnitude; or
   iii. a preselected frequency component thereof having a preselected minimum amplitude.

14. The method of claim 12 including the additional step of maintaining by electronic timing means the inhibition of said second output signal for a preselected duration once said undesirable electrical characteristic is detected.

15. The method of claim 12 including the additional step of providing a second sensory stimulus capable of stimulating at least one of the senses of said organism whenever said method is inhibited;
   whereby said organism is informed that at least one undesirable electrical characteristic has been detected.

16. The method of claim 1 including, following step (a) thereof, the additional steps of:
   i. passing at least one of said bioelectrical signals through second electronic means responsive to the presence of at least one electrical characteristic of interest in the waveform thereof and adapted to provide a third output signal which is an electrical analog of said characteristic of interest, if present;
   ii. transducing said third output signal into a sensory stimulus which is also an analog of said characteristic of interest, said stimulus being capable of stimulating at least one of the senses of said organism, said analog sensory stimulus being presented to said organism as a reward for producing said corresponding bioelectrical signal having said characteristic of interest;
   iii. detecting the presence of at least one undesirable electrical characteristic in the waveform of at least one of said bioelectrical signals;
   iv. before steps (d) and (ii), inhibiting the appearance of said second and third output signals by electronic inhibit means when and if said undesirable electrical characteristic is detected;
   whereby, said method is inhibited by inhibiting the presentation of said discrete and analog sensory stimuli to said organism.

17. The method of claim 16 wherein said undesirable electrical characteristics in said bioelectrical signal is;
   i. a particular frequency component thereof;
   ii. an amplitude thereof greater than a preselected mangitude; or
   iii. a particular frequency component thereof having a preselected minimum amplitude.

18. The method of claim 16 including the additional step of maintaining by electronic timing means the inhibition of said second and third output signals for a preselected duration once said undesirable electrical characteristic is detected.

19. A method of controlling the nervous system of a living organism comprising the steps of:
   a. detecting one or more bioelectrical signals from one or more topological locations in said organism's nervous system;
   b. passing said one or more bioelectrical signals through a plurality of electronic means responsive to the presence of at least one electrical characteristic of interest in the waveform of a bioelectrical signal, each of said responsive means being adapted to provide a first output signal whenever said electrical characteristic of interest is present, wherein said electrical characteristic of interest in any of said bioelectrical signals is:
   i. a preselected frequency component thereof;
   ii. an amplitude thereof greater than a preselected minimum; or
   iii. a preselected frequency component thereof having a preselected minimum amplitude;
   c. determining by electronic logic means when said plurality of first output signals, or any subset thereof, is present or absent in a predetermined manner indicative of a desired condition of said organism's nervous system, said logic means being adapted to provide a second output signal when said desired condition is indicated;

d. passing said second output signal through a timing circuit adapted to detect whether said second output is present for a preselected minimum duration and to pass said second output signal only if it persists for said minimum duration;

e. detecting the presence of at least one undesirable electrical characteristic in the waveform of at least one of said bioelectrical signals;

f. inhibiting the appearance of said second output signal by electronic inhibit means when and if said undesirable electrical characteristic is detected;

g. transducing said second output signal into a discrete sensory stimulus capable of stimulating at least one of the senses of said organism; and h. causing said organism to concentrate mentally so as to produce or change the state of said discrete sensory signal;

whereby said organism is trained to alter the waveform pattern of said one or more bioelectrical signals, said discrete sensory stimulus being presented to said organism as a reward for producing or suppressing said electrical characteristics of interest in said one or more signals, and for suppressing said undesirable electrical characteristic, thereby achieving said desired condition of said nervous system.

20. A system for controlling the nervous system of a living organism comprising:

a. one or more means for detecting a bioelectrical signal disposed at one or more topological locations in the nervous system of said organism;

b. a plurality of electronic means responsive to the presence of at least one electrical characteristic of interest in the waveform of a bioelectrical signal, each of said responsive means being electrically coupled to one of said bioelectrical signal detection means and being adapted to provide at its output a first output signal whenever said electrical characteristic of interest is present;

c. electronic logic means for determining when said plurality of first output signals, or any subset thereof, is present or absent in a predetermined manner indicative of a desired condition of said organism's nervous system, said logic means having a plurality of inputs electrical coupled to corresponding outputs from said plurality of responsive means; and d. means for transducing said second output signal into a discrete sensory stimulus capable of stimulating at least one of the senses of said organism, said transducing means being electrically coupled to the output of said logic means;

whereby said organism is trained to alter the waveform pattern of said one or more bioelectrical signals by concentrating so as to produce or change the state of said discrete sensory stimulus, said sensory stimulus being presented to said organism as a reward for producing or suppressing said electrical characteristics of interest in said one or more signals, thereby achieving said desired condition of said nervous system.

21. The system of claim 20 wherein said means for detecting said bioelectrical signals are electrodes adapted to be coupled to said organism.

22. The system of claim 20 wherein each of said plurality of responsive means is electrically coupled to said bioelectrical signal detection means through means for amplifying said signal.

23. The system of claim 20 wherein at least one of said responsive means comprises a bandpass filter responsive to a preselected frequency component of said bioelectrical signal.

24. The system of claim 20 wherein at least one of said responsive means comprises means for sensing voltage amplitude responsive to an amplitude of said bioelectrical signal which is greater than a preselected minimum.

25. The system of claim 20 wherein at least one of said responsive means comprises a bandpass filter electrically coupled to means for sensing voltage amplitude, said combination thereof being responsive to a preselected frequency component of said bioelectrical signal having a preselected minimum amplitude.

26. The system of claim 20 wherein one bioelectrical signal detection means is disposed at one topological location in said organism's nervous system and electrically coupled to each of said plurality of responsive means.

27. The system of claim 20 wherein a plurality of bioelectrical signal detection means are disposed at a plurality of topological locations in said organism's nervous system and each is electrically coupled to a corresponding one of said plurality of responsive means.

28. The system of claim 20 wherein a plurality of bioelectrical signal detection means are disposed at a plurality of topological locations in said organism's nervous system, and wherein at least one of said detection means is electrically coupled to at least two of said plurality of responsive means, and said other detection means, if any, are each electrically coupled to one of said plurality of responsive means.

29. The system of claim 20 including in addition thereto means for sensing the duration of said second output signal, said duration sensing means being electrically coupled between said logic means and said transducing means and being adapted to pass said second output signal only if it is present for a said preselected minimum duration.

30. The system of claim 20 wherein said logic means is adapted to provide said second output signal when said plurality of first output signals, or any subset thereof, are present or absent concurrently.

31. The system of claim 20 wherein said logic means comprises means for timing intervals, said timing means being adapted to enable the determination of whether at least one of said plurality of first output signals is present or absent during a preselected interval following the presence or absence of at least one other of said first output signals, said logic means being adapted to provide said second output signal only if said interval condition is satisfied.

32. The system of claim 20 having in addition thereto electronic means for timing the duration of the presentation of said sensory stimulus to said organism, said timing means being electrically coupled to said transducing means.

33. The system of claim 20 having in addition thereto;

i. at least one second means responsive to the presence of an electrical characteristic of interest in the waveform of a bioelectrical signal and adapted to provide a third output signal which is a unipolar electrical analog of said characteristic of interest, if present, said second responsive means being electrically coupled to one of said bioelectrical signal detection means; and ii. second means for transducing said third output signal into a sensory stimulus capable of stimulating at least one of the senses of said organism, said stimulus also being an analog of said characteristic of interest and being electrically coupled to the output of said second responsive means, whereby said analog sensory stimulus is presented to said organism as a reward for producing said corresponding bioelectrical signal with said characteristic of interest.

34. The system of claim 20 having in addition thereto:

i. at least one means for detecting the presence of an undesirable electrical characteristic in the waveform of a bioelectrical signal and adapted to provide at its output an inhibit signal whenever said undesirable characteristic is detected, said undesirable characteristic detection means being electrically coupled to one of said bioelectrical signal detection means; and ii. means for inhibiting the appearance of said second output signal, said inhibit means being responsive to said inhibit signal, the input of said inhibit means being electrically coupled to said undesirable characteristic detection means and the output thereof being electrically coupled to each of said plurality of responsive means, whereby, the presentation of said discrete sensory stimulus to said organism is inhibited.

35. The system of claim 34 wherein said means for detecting the presence of an undesirable characteristic in the waveform of a bioelectrical signal comprises:
i. an attenuator;
ii. a bandpass filter;
iii. means for rectifying;
iv. means for integrating; and
v. means for sensing voltage ampltiude, said components being electrically coupled in series.

36. The system of claim 34 having in addition thereto a timing circuit adapted to control the duration for which said inhibit means is operative once said undesirable electrical characteristic is detected, said timing circuit being electrically coupled to said inhibit means.

37. The system of claim 34 having in addition thereto means for transducing said inhibit signal into a second discrete sensory stimulus capable of stimulating at least one of the senses of said organism;

whereby, said organism is informed that at least one undesirable electrical characteristic has been detected.

38. The system of claim 34 having more than one means for detecting the presence of an undesirable electrical characteristic and a corresponding number of means for transducing said inhibit signal into a discrete sensory stimulus, whereby, said organism is informed, by a separate stimulus, whenever any of said undesirable characteristics has been detected.

39. The system of claim 20 having in addition thereto;

i. at least one second means responsive to the presence of an electrical characteristic of interest in the waveform of a bioelectrical signal and adapted to provide a third output signal which is a unipolar electrical analog of said characteristic of interest, if present, said second responsive means being electrically coupled to one of said bioelectrical signal detection means;

ii. second means for transducing said third output signal into a sensory stimulus capable of stimulating at least one of the senses of said organism, said stimulus also being an analog of said characteristic of interest and being electrically coupled to the output of said second responsive means, iii. at least one means for detecting the presence of an undesirable electrical characteristic in the waveform of a bioelectrical signal and adapted to provide at its output an inhibit signal whenever said undesirable characteristic is detected, said undesirable characteristic detection means being electrically coupled to one of said bioelectrical signal detection means; and iv. means for inhibiting the appearance of said second and third output signals, said inhibit means being responsive to said inhibit signal, the input of said inhibit means being electrically coupled to said undesirable characteristic detection means and the output thereof being electrically coupled to each of said plurality of responsive means, whereby, the presentation of said discrete and analog sensory stimuli to said organism is inhibited.

40. The system of claim 39 having in addition thereto a timing circuit adapted to control the duration for which said inhibit means is operative once said undesirable electrical characteristic is detected, said timing circuit being electrically coupled to said inhibit means.

41. A system for controlling the nervous system of a living organism comprising:

a. one or more electrodes adapted to be coupled to one or more topological locations in the nervous system of said organism and to detect one or more bioelectrical signals therein;

b. a plurality of electronic means responsive to the presence of at least one electrical characteristic of interest in the waveform of a bioelectrical signal, each of said responsive means being electrically coupled to one of said electrodes through amplifying means and being adapted to provide at its output a first output signal whenever said electrical characteristic of interest is present;

c. electronic logic means for determining when said plurality of first output signals, or any subset thereof, is present or absent in a predetermined manner indicative of a desired condition of said organism's nervous system, said logic means having a plurality of inputs electrically coupled to corresponding outputs from said plurality of responsive means;

d. means for sensing the duration of said second output signal, said duration sensing means being electrically coupled to the output of said logic means and being adapted to pass said second output signal only if it is present for a said preselected minimum duration;

e. at least one means for detecting the presence of an undesirable electrical characteristic in the waveform of a bioelectrical signal and adapted to provide at its output an inhibit signal whenever said undesirable characteric is detected, said undesirable characteristic detection means being electrically coupled to one of said bioelectrical signal detection means;

f. means for inhibiting the appearance of said second output signal, said inhibit means being responsive to said inhibit signal, the input of said inhibit means being electrically coupled to said undesirable characteristic detection means and the output thereof being electrically coupled to each of said plurality of responsive means and to said duration sensing means; and g. means for transducing said second output signal into a discrete sensory stimulus capable of stimulating at least one of the senses of said organism, said transducing means being electrically coupled to the output of said logic means;

whereby said organism is trained to alter the waveform pattern of said one or more bioelectrical signals by concentrating so as to produce or change the state of said discrete sensory stimulus, said sensory stimulus being presented to said organism as a reward for producing or suppressing said electrical characteristics of interest in said one or more signals, and for suppressing said undesirable electrical characteristic, thereby achieving said desired condition of said nervous system.

* * * * *

UNITED STATES PATENT AND TRADEMARK OFFICE
CERTIFICATE OF CORRECTION

PATENT NO. : 3,967,616
DATED : July 6, 1976
INVENTOR(S) : Sidney A. Ross

It is certified that error appears in the above-identified patent and that said Letters Patent are hereby corrected as shown below:

In the Abstract, line 6, insert a space between "specific" and "topological".

Column 2, line 19, "in" should be "is".

Column 7, line 1, "oneshot" should be "one-shot".

Column 7, line 8, insert--a--between "contemplates" and "coincidence".

Column 7, line 59, "sensor" should be "sensory".

Column 10, line 32, "tidisplay" should be "ti-display".

Column 12, line 52, "our" should be "or".

Column 15, line 52, "electrical" should be "electrically".

Signed and Sealed this

Tenth Day of June 1980

[SEAL]

Attest:

SIDNEY A. DIAMOND

*Attesting Officer*  *Commissioner of Patents and Trademarks*